(12) United States Patent
Ericksen et al.

(10) Patent No.: US 6,731,983 B2
(45) Date of Patent: May 4, 2004

(54) PACEMAKER HAVING ADAPTIVE ARRHYTHMIA DETECTION WINDOWS

(75) Inventors: James H. Ericksen, North Oaks, MN (US); Robert A. Betzold, Fridley, MN (US); Catherine R. Condie, Shoreview, MN (US); Jeffrey M. Gillberg, Coon Rapids, MN (US); Robert W. Stadler, Shoreview, MN (US); John C. Stroebel, Blaine, MN (US); Troy E. Jackson, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 228 days.

(21) Appl. No.: 10/082,981

(22) Filed: Feb. 25, 2002

(65) Prior Publication Data

US 2003/0083705 A1 May 1, 2003

Related U.S. Application Data

(63) Continuation-in-part of application No. 10/003,935, filed on Oct. 30, 2001.

(51) Int. Cl.[7] .................................................. A61N 1/36

(52) U.S. Cl. ......................................................... 607/14
(58) Field of Search ....................................... 607/4–31

(56) References Cited

U.S. PATENT DOCUMENTS

| 4,228,308 A | 10/1980 | Mac Laury .................. 568/726 |
| 4,428,378 A | 1/1984 | Anderson et al. ..... 128/419 PG |
| 4,467,807 A | 8/1984 | Bornzin ................. 128/419 PG |
| 4,951,667 A | 8/1990 | Markowitz et al. ... 128/419 PG |

OTHER PUBLICATIONS

Kappenberger et al., "Rate Responsive Dual Chamber Pacing," PACE, vol. 9, pp. 987–991 (Nov.–Dec. 1986).

Primary Examiner—Scott M. Getzow
(74) Attorney, Agent, or Firm—Girma Wolde-Michael; Michael C. Soldner

(57) ABSTRACT

A device-implemented software system operates a detection window and adjusts PAV as needed after confirming the presence or detection of evidence of an arrhythmia. The detection window is monitored based on a preferred length. If the detection window is shorter than required, intervals are adjusted for a specific pacing rate. Further, the software system provides means for selecting detection over pacing based on an analysis of a preferred length in the presence of evidence of an arrhythmia.

9 Claims, 9 Drawing Sheets

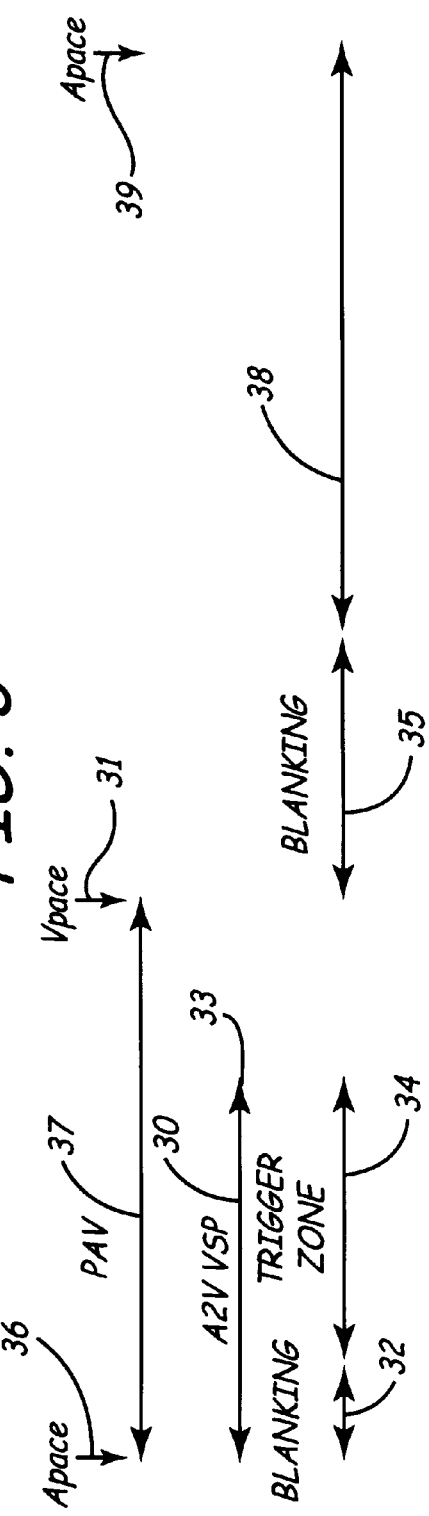
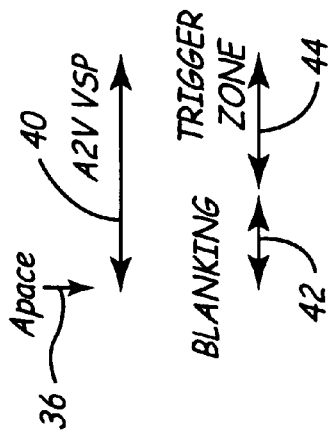

PACEMAKER HAVING ADAPTIVE ARRHYTHMIA DETECTION WINDOWS

RELATED APPLICATIONS

This application is a continuation-in-part and claims priority to U.S. patent application Ser. 10/003,935 filed Oct. 30, 2001, and incorporates the specification and drawings in their entireties by reference herein.

FIELD OF THE INVENTION

The present invention relates generally to cardiac pacemakers. More particularly, the present invention relates to cardiac pacemakers having improved methods for detecting arrhythmias.

BACKGROUND OF THE INVENTION

An arrhythmia is a heart rhythm disorder which interferes with the life sustaining blood pumping action of the heart. Examples of arrhythmias include ventricular tachycardia and atrial tachycardia. Ventricular tachycardia effects the lower chambers of the heart, the ventricles, and atrial tachycardia effects the upper chambers of the heart, the atria. Ventricular tachycardia is a rapid heart beat initiated within the ventricles, characterized by three or more consecutive premature ventricular beats. Ventricular tachycardia is a potentially lethal arrhythmia, as it may cause the heart to become unable to pump adequate blood through the body. Companies such as Medtronic, Inc., have developed implantable pacemakers which may be used to successfully treat ventricular tachycardia by delivering ventricular pacing pulses to the heart when ventricular tachycardia is detected.

Dual chamber pacing modes have been widely adopted for pacing therapy. Among the dual chamber operating modes is the "DDD" mode, which can pace an atrium and a ventricle, senses both the atrium and the ventricle, and can either inhibit or trigger pacing stimuli for both chambers. This mode has a sensor augmented variant mode called "DDDR", where the "R" stands for rate-adaptive or rate modulation.

A DDD pacemaker includes an atrial sense amplifier to detect atrial depolarizations of the heart, and a ventricular sense amplifier to detect ventricular depolarizations of the heart. If the atrium of the heart fails to beat within a predefined time interval (atrial escape interval), the pacemaker supplies an atrial stimulus to the atrium through an appropriate lead system. Following an atrial event (either sensed or paced) and an atrioventricular (A-V or A2V) interval, the pacemaker supplies a ventricular pacing stimulus to the ventricle through an appropriate lead system, if the ventricle fails to depolarize on its own. Pacemakers which perform this function have the capability of tracking the patient's natural sinus rhythm and preserving the hemodynamic contribution of the atrial contraction over a wide range of heart rates.

Various types of pacemakers are disclosed in the prior art, and are presently in widespread use. The pacing literature has documented the different types of pacemakers and their characteristics extensively. A summary of the evolution and characteristics of pacemaker types, and specifically different types of dual chamber pacemakers, is set forth in U.S. Pat. No. 4,951,667, which is incorporated herein by reference.

Another and more recent advance in the field of cardiac pacing systems is that of the rate responsive pacemaker which increases cardiac output in response to exercise or other body demands. Such pacemakers may control pacing rate based upon sensing any one or a combination of different body parameters such as body activity, blood pH, respiratory rate, QT interval or historical atrial activity. See, for example, U.S. Pat. No. 4,428,378, (Anderson et al.), disclosing a pacemaker which varies pacing rate in response to sensed patient activity; and U.S. Pat. No. 4,228,308, (Rickards), which discloses controlling pacing rate in response to Q-T interval. Additionally, rate responsive control has been integrated into dual chamber pacing systems, e.g., DDDR and DDIR systems. See "Rate Responsive Dual Chamber Pacing" in PACE, vol. 9, pp. 987–991;U.S. Pat. No. 4,467,807, Bornzin; and the above-noted U.S. Pat. No. 4,951,667.

Background information directly related to the present invention may be discussed in greater detail. The atrium may be paced with an A-pace. The energy from the A-pace may be sensed by the ventricle amplifier as a V-sense event. This is referred to as an over-sense or cross-chamber sensing. It is not really a contraction of the ventricle, but is rather the electrical activity of the atrium being detected by the sensor in the ventricle. In this situation, the ventricle may not have actually contracted. If the V-sense event is too close to the A-pace event, a ventricular safety pace (VSP) stimulation pulse is given to the ventricle, in case the V-sense was actually an indication of a premature ventricular contraction, which might continue as ventricular tachycardia.

In many patients, it would be desirable to wait until closer in time to the expected time of a natural ventricular contraction. However, waiting too long would put the VSP pulse at about the same point in time as the T-wave, which would be undesirable, as pacing in the middle of the T-wave may cause an arrhythmia. The VSP pulse is given because of a premature V-sense, which is believed to not be an indication of an actual ventricular contraction. If the V-sense reflected a real ventricular contraction, there would be nothing seen from the ventricle until the next natural event. Therefore, waiting a long period would gain nothing. If the V-sense was an over-sense, then waiting for the V-sense reflecting an actual ventricular contraction would require waiting too long, putting any required V-pace too close to the T-wave. Thus, in this situation, while it is not known that the V-sense reflected an actual premature ventricular contraction, it is desirable that the ventricle contract. Therefore the VSP pulse will be generated to ensure that the ventricle contracts.

When a pacemaker is operated in DDD mode, the atrium is paced in the absence of a sensed natural event. After the A-pace, there is a time period, a trigger window, within which a V-sense may be detected. If a V-sense is detected during this window, then a VSP pulse will be scheduled, at the end of the VSP timing window or interval.

In one example, where a desired pacing rate of about 120 beats per minute is desired, the VSP, if it is to occur at all, will be scheduled at about 60 milliseconds after the A-pace. In the example where a slower desired pacing rate of about 60 beats per minute is desired, the VSP, if it is to occur at all, is scheduled at about 110 milliseconds after the A-pace. The VSP is normally scheduled no longer than about 80 milliseconds after the V-sense, to avoid being too close to the T-wave. In the absence of any V-sense event within the trigger window after the A-pace, the next scheduled V-pace would not normally occur for a longer period, for example, about 150 milliseconds. This interval from the A-pace to the V-pace can be based on the PAV interval.

In a paced, cardiac cycle, there may be three blanking periods where the pacemaker is unable to sense arrhythmias. The first blanking period follows the A-pace. The second blanking period follows a V-sense, as it is undesirable for the pacing device to double count the V-sense event. The third blanking period follows the V-pace. Thus,, if there is a ventricular arrhythmia occurring at a fast rate, the pacing device may see only every other beat, resembling a normal heart beat.

It would be desirable to provide an algorithm that favors detection over pacing in a stronger way than is proposed in the previous disclosure. It is further desirable to provide a system in which the detection window is long enough contemporaneous with evidence of an arrhythmia. It would also be desirable to provide a long interval between a ventricular event and the next scheduled atrial pace such that the atrial pace does not interfere, with detection.

SUMMARY OF THE INVENTION

The present invention provides improved methods for cardiac pacing that may find particular use in pacing situations having high pacing rates that would otherwise have substantially shortened windows for detecting arrhythmias and/or pacing situations forced to accept slow pacing rates to maintain long windows for detecting arrhythmias.

In accordance with the improved aspect of the invention, in the event there is detection or an evidence of an arrhythmia, a device-implemented software system opens a detection window. Subsequently, the software system checks to see if there is a need to adjust PAV. If the detection window is not long enough, the software sets PAV to a minimum. Thereafter, the detection window is checked to see if it is long enough. If the detection window is found to be shorter than required, the TLRI (temporary lower rate interval) is changed to the temporary lower rate interval for the pacing rate.

Yet another aspect of the invention provides a preferential selection of detection over pacing. Specifically, where there is evidence of an arrhythmia, the detection window is checked to see if it is long enough. This is to ensure that the time between a ventricular event and the next scheduled atrial pace is kept long enough so that the atrial pace does not interfere with detection.

DESCRIPTION OF THE DRAWINGS

FIG. 3 is a schematic, timing diagram of a cardiac pacing cycle having a fixed A2V VSP interval and a cross chamber blanking interval, followed by a trigger zone, where the Rigger zone terminates at the same point in time as the A2V VSP interval;

FIG. 4 is a schematic, timing diagram of a cardiac pacing cycle similar to that of FIG. 3, but having a shortened A2V VSP interval, and a shortened trigger zone which terminates at the same point in time as the A2V VSP interval;

FIG. 5 is a timing diagram similar to that of FIG. 3, but having a shortened trigger zone which terminates earlier in time that the A2V VSP interval;

DETAILED DESCRIPTION OF THE PREFERRED EMBODIMENTS

Figure 1:
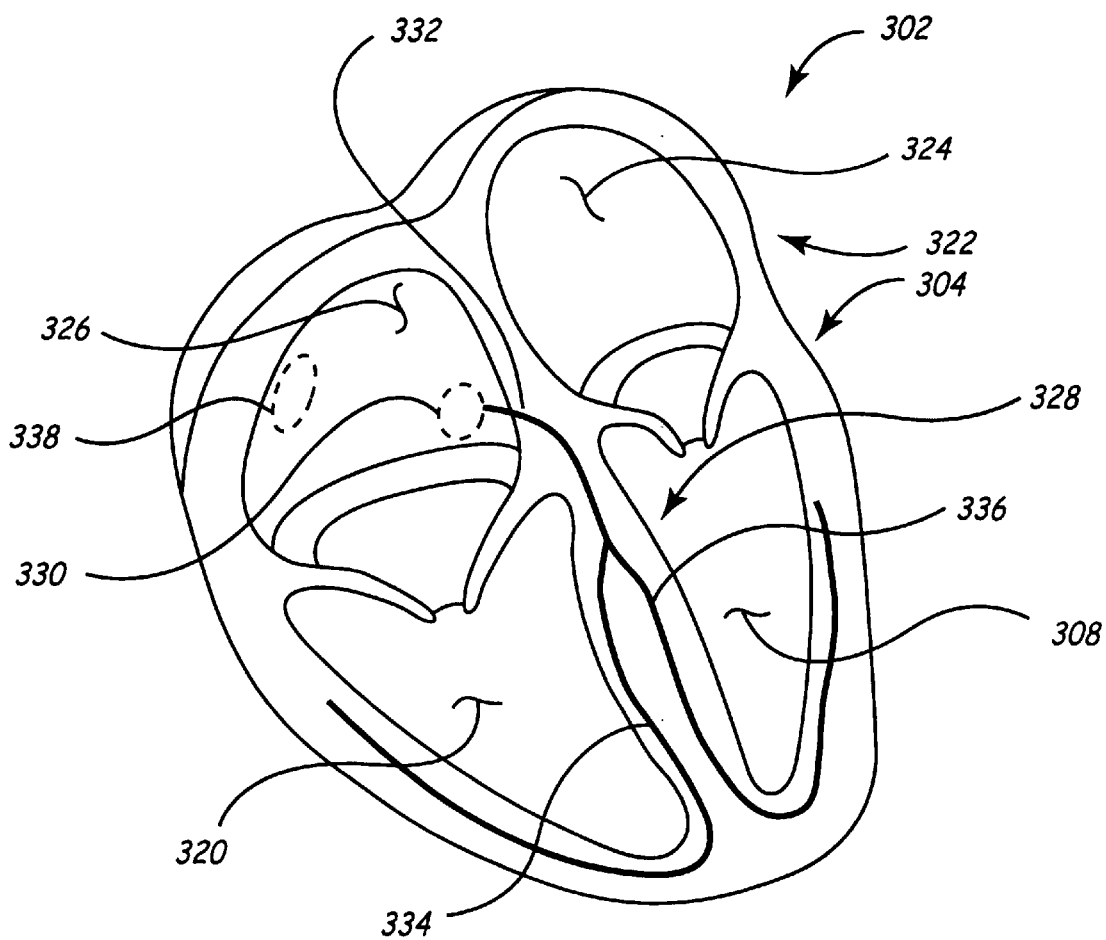
FIG. 1 is a cross-sectional view of a heart having ventricles and atria.

The following detailed description should be read with reference to the drawings, in which like elements in different drawings are numbered identically. The drawings, which are not necessarily to scale, depict selected embodiments and are not intended to limit the scope of the invention. Several forms of invention have been shown and described, and other forms will now be apparent to those skilled in art. It will be understood that embodiments shown in drawings and described above are merely for illustrative purposes, and are not intended to limit scope of the invention as defined in the claims which follow:

FIG. 1 is a cross-sectional view of a heart 302 having ventricles 304 and atria 322. Ventricles 304 of heart 302 include a left ventricle 308 and a right ventricle 320, and atria 322 of heart 302 include a left atrium 324 and a right atrium 326. In FIG. 1, it may be appreciated that heart 302 includes a conductive path 328 extending between atria 322 and ventricles 304. In heart 302, conductive path 328 includes an atrioventricular (AV) node 330, a bundle of His 332, a right bundle branch 334, and a left bundle branch 336.

Heart 302 also includes a sinoatrial (SA) node 338. In a healthy heart, the SA node acts as a natural pacemaker controlling the life sustaining blood pumping action of the heart. At an appropriate time, an electrical impulse arising from the SA node is transmitted to the right and left atrial chambers. This impulse causes muscle tissue surrounding the atrium to depolarize and contract which generates an electrical signal known as a P-wave. The same electrical impulse arising from the SA node also travels to the right and left ventricles through the atrioventricular (AV) node. The impulse received by the AV node is transmitted through the bundle of His, the right bundle branch, the left bundle branch, and a plurality of Purkinje fibers that encompass most of the endocardial surface of the ventricles. The ventricular muscle tissue depolarizes, then contracts. This forces blood held in the ventricles through the arteries and to various body locations. This action is repeated in a rhythmic cycle in which the atrial and ventricular chambers alternately contract and pump, then relax and fill.

Figure 2:
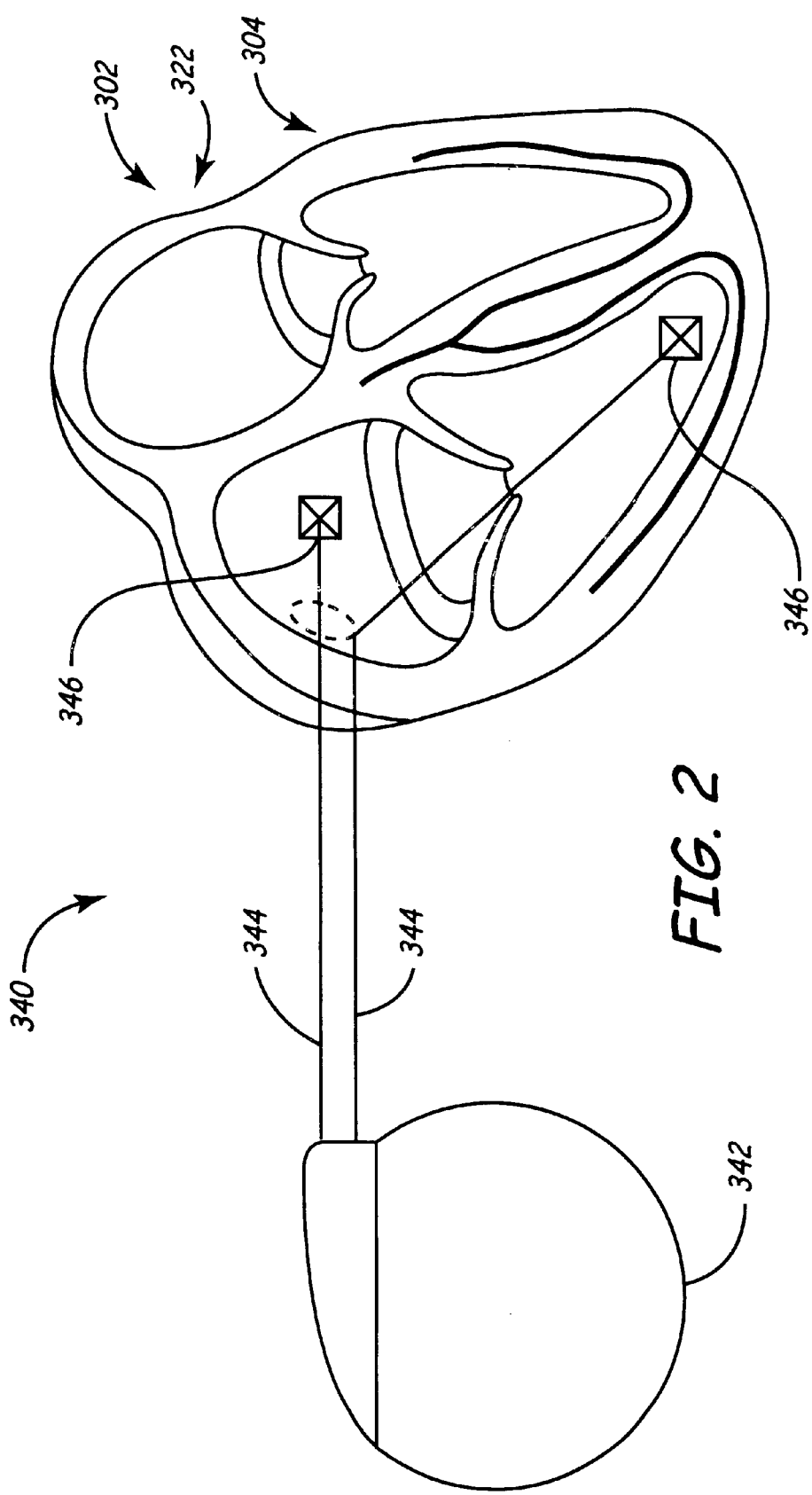
FIG. 2 is a diagrammatic view of a pacing system in accordance with the present invention.

FIG. 2 is a diagrammatic view of a pacing system 340 in accordance with the present invention. Pacing system 340 includes a pacemaker 342 that is coupled to heart 302 of FIG. 1 by a plurality of leads 344 and electrodes 346. Pacemaker 342 may be used to treat a heart in which the natural pacing system has ceased performing properly. Pacemaker 342 may have a single electrode operation in which pacing current flows between an electrode 346 and a housing of pacemaker 342. Pacemaker 342 may also have a dual electrode operation in which pacing current flows between two or more electrodes.

Some methods in accordance with the present invention may include the step of severing the conductive path between atria 322 and ventricles 304. In some methods, the step of severing the conductive path may include the step of ablating the AV node of a heart. The step of ablating the AV node may be accomplished, for example, using a catheter including an ablation electrode coupled to a source of radio or other form of frequency energy. By comparing FIG. 1 and FIG. 2, it may be appreciated that the AV node of heart 302 has been ablated in the embodiment of FIG. 2.

FIG. 3 illustrates a standard method of pacing using the ventricular safety pacing (VSP) feature. The ventricular safety pace is a ventricular pace event that is delivered after an atrial pace, if a ventricular sense is detected in a short window after the atrial pace. In this method, there is a fixed atrial-to-ventricular (A2V) ventricular safety pacing (VSP) interval. In the method illustrated, the A2V VSP interval 30 is 110 ms. long. The A2V interval includes a 30 ms. cross chamber blanking zone 32 and an 80 ms. trigger zone 34. The A2V VSP interval 30 begins with an atrial pace 36. If a ventricular sensed event occurs in the trigger zone, the device delivers a ventricular safety pace at the end of the A2V VSP interval 33.

FIG. 3 also illustrates the paced arterial to ventricular (PAV) interval at 37, extending from Apace 36 to ventricular pace (Vpace) 31. A Vpace blanking interval 35 follows Vpace 31, which is followed by a V2A detection interval 38. A second Apace 39 ends one cardiac cycle and can define the cardiac A2A interval, along with the V2V interval.

The arrhythmia detection process may be blinded from the atrial pace 36 to the end of the ventricular pace blanking 35 that starts with the ventricular safety pace. This is not a problem as long as the interval between the ventricular safety pace at 33 and the next atrial pace 39 is long enough to allow an arrhythmic event to be sensed before the next atrial pace. One way of minimizing the impact of ventricular safety pacing on detection of a ventricular sensed event is to shorten the A2V VSP interval. In FIG. 3, the cross-chamber blanking interval 32 is 30 ms. long.

FIG. 4 illustrates a method utilizing a shorter A2V VSP interval than that of FIG. 3. The blanking interval 42 is again 30 ms. long, followed in this method by a shorter, 40 ms. long trigger zone 44. Together, blanking zone 42 and trigger zone 44 form an A2V VS P timing interval 40 having a duration of about 70 ms. One problem with this method is that at slower pacing rates, an A2V interval less than 110 ms. may not be desirable.

It may be better yet for the patient to have longer A2V VSP intervals at the faster rates. In cases where there are very few VSP paces, detection will work with the longer VSP. In these cases, an algorithm that switched to a VSP like that of FIG. 5 below, at high pacing rates, would decrease the number of VSP events. If multiple VSP events occurred in a specified amount of time, the device would switch to the VSP method described in FIG. 4.

FIG. 5 illustrates a ventricular safety pacing method having a short trigger zone. The ventricular safety pacing method of FIG. 5 includes an A2V VSP timing interval 50, having a length of 110 ms., terminating at a VSP pace point 58, where a VSP pace is delivered if a ventricular event is sensed by the device within the trigger zone. A blanking interval of 30 ms. is indicated at 52, followed by a 40 ms. long trigger zone indicated at 54. The blanking interval begins with atrial pacing event 56, as before.

Figure 6:
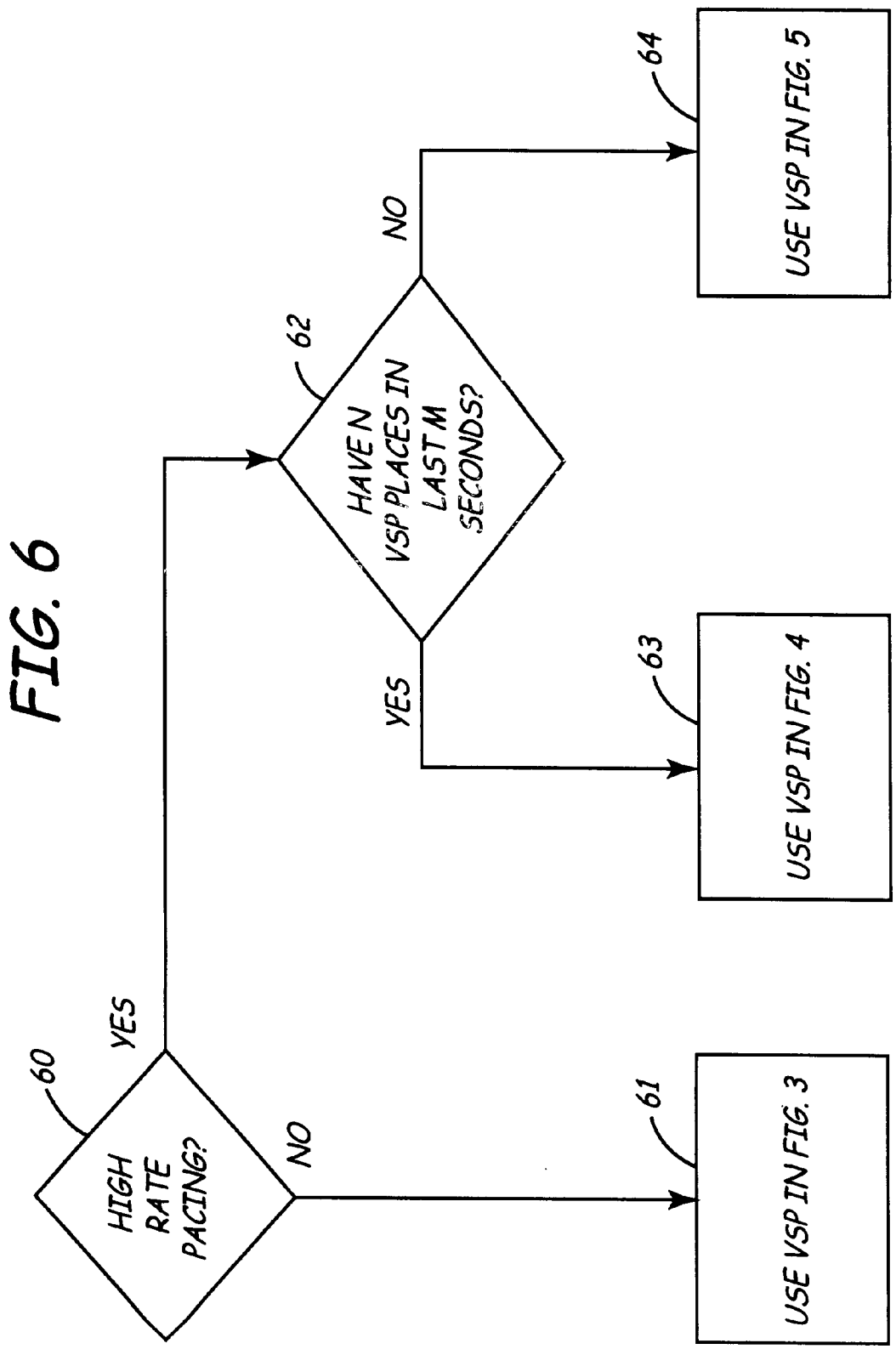
FIG. 6 is a high level flow chart of a method for switching between the cardiac pacing methods of FIGS. 3, 4, and 5.

One method according to the present invention may be briefly described with reference to FIG. 6. If a high rate pacing is not desired at step 60, then the ventricular safety pacing method 61 of FIG. 3 is used. If a high rate of pacing is desired at step 60, then it must be determined at step 62 whether N VSP paces have occurred in the last M seconds.

In other words, determine whether a limit number N of paces occurred within a time window M. If a sufficient number of VSP paces have occurred within the time window, then the VSP method of FIG. 4 is used at 63. On the other hand, if an insufficient number of VSP have not occurred in the time window, then the VSP method of FIG. 5 is used at 64. This overall method can decrease the adverse effect, if any, that VSP events have on detection at high pacing rates. These adverse effects on detection can be eliminated if the device decreases the pacing rate in the presence of VSP events, and increases the pacing rate in the absence of VSP events.

Figure 7:
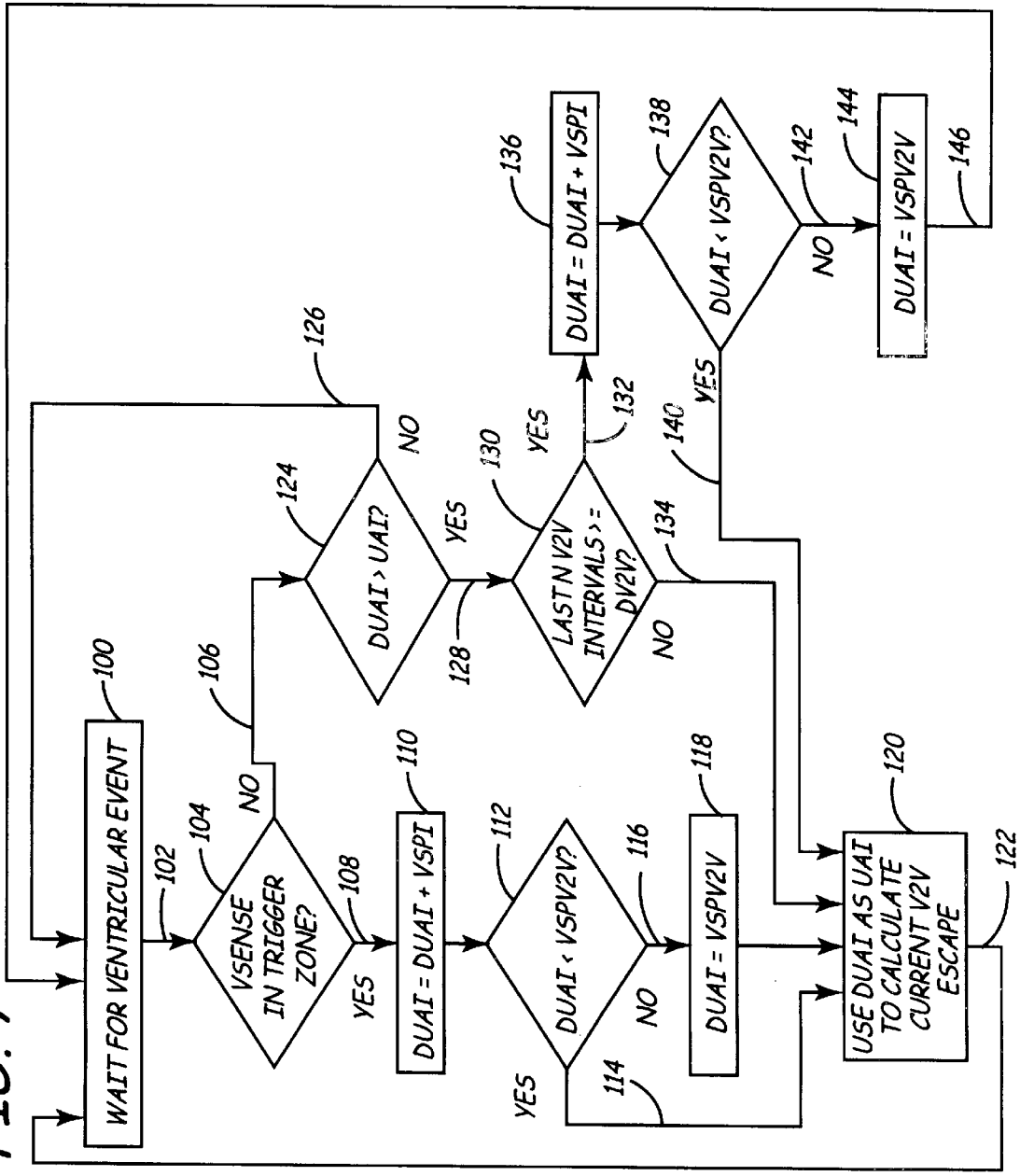
FIG. 7 is a flow chart of a method for adapting the overall pacing interval in the presence of VSP.

FIG. 7 illustrates a method for adapting the pacing rate in the presence of ventricular safety pacing. As used herein, "V2V interval" is defined to be the interval between the previous ventricular event to the current ventricular event. As used herein, "ventricular event" includes Vsenses and Vpaces, but not ventricular safety paces. In step 100, the method waits for a ventricular event. Upon detection of a ventricular event, either a V-sense or a V-pace, but not a VSP, path 102 is followed, and step 104 executed. At step 104, a determination is made as to whether the ventricular event was a V-sense and within the trigger zone. If the ventricular event detected was a V-sense within the trigger zone, then path 108 is followed. Otherwise, the ventricular event detected is paced, and path 106 is followed. If path 106 is followed, then step 124 is executed.

In step 124, a determination is made as to whether the dynamic upper activity interval (DUAI) is greater than the upper activity interval (UAI). The UAI is the programmed minimum V2V escape for brady pacing. The DUAI is the dynamic upper activity level. This interval is greater than or equal to UAI and less than or equal to VSPV2V. If the DUAI is not greater than UAI at 124, then DUAI is already at minimum, so there is no need to check further with respect to decreasing DUAI. In this situation, path 126 is followed and step 100 is executed again, waiting for the next ventricular event. If the DUAI is greater than the UAI, then path 128 is followed from step 124 to step 130. In step 130, a determination is made as to whether all of the last N V2V intervals are greater than or equal to DV2V, the minimum V2V interval ending in a ventricular pace that is long enough such that it will not interfere with detection. If all of the last N V2V intervals are not greater than or equal to DV2V at 130, then path 134 is followed and step 120 is executed.

In step 120, the dynamic upper activity interval (DUAI) is used as the upper activity interval (UAI) in calculating the current V2V escape. After execution of step 120, path 122 is followed, returning control to step 100 to wait for another ventricular event.

At decision step 104, if the ventricular event is in a trigger zone, path 108 is followed to execute step 110. In step 110, the dynamic upper activity interval (DUAI) is increased by an increment VSPI, where VSPI is the increment to DUAI when a VSP event takes place. After incrementing DUAI, step 112 is executed.

In decision step 112, a determination is made as to whether the dynamic upper activity interval (DUAI) is less than VSPV2V, the minimum V2V escape following a ventricular safety pace that will insure the safety pace does not interfere with arrhythmia detection. If the dynamic upper activity interval (DUAI) is not less than this minimum V2V escape, VSPV2V at 112, then path 116 is followed and step 118 is executed. In step 118, the dynamic upper activity interval (DUAI) is set equal to the minimum V2V escape previously discussed VSPV2V. After execution of step 118, step 120 is executed, followed by step 100 as previously discussed.

Referring again to step 130, execution is analyzed for the case where all of the previous N V2V intervals were greater than or equal to the minimum V2V interval DV2V, in which case path 132 is followed to step 136. N is equal to 10 seconds in some methods. Step 130 may be viewed as determining whether there are all recent short V2V intervals, meaning normal sinus rhythm. If there has recently been normal sinus, then DUAI can be decreased, increasing the pacing rate. In step 136, the dynamic upper activity interval (DAUI) is decreased by the amount VSPD. After DAUI is decreased in step 136, execution proceeds to a decision step 138. In decision step 138, a determination is made as to whether the dynamic upper activity interval (DUAI) is greater than the upper activity interval that is the programmed minimum V2V escape for brady pacing UAI. If the dynamic upper activity interval (DUAI) is greater than the upper activity interval (UAI), then path 140 is followed and step 120 is executed as previously discussed. If the dynamic upper activity interval is not greater than the upper activity interval, then path 142 is followed, and step 144 is executed. In step 144, the upper activity interval (DUAI) is set equal to the upper activity interval (UAI). After execution of step 144, path 146 is followed, returning execution to step 100 to wait for the next ventricular event.

The method of the present invention gradually slows the pacing rate to insure proper detection of arrhythmia. In the absence of arrhythmia and/or any cross-talk, the method allows the pacing rate to gradually return to the desired brady pacing rate. The rate at which the intervals are changed is controlled by setting the parameters VSPI and VSPD, where VSPI is the increment added when a VSP event takes place. VSPD is the decrement which is subtracted when a VSP does not take place.

In another aspect of the invention, the PAV interval length may be adaptively varied. In some situations, it is advantageous to set the time from an atrial pace to the next scheduled ventricular pace PAV to a long value, even at fast pacing rates. By doing this, the patient is given a better chance to receive a conducted ventricular contraction. This may make detection arrhythmias difficult. Detection may not know whether a ventricular event with a short V2V interval and an atrial pacing event in the V2V interval, should be treated as a conducted event or as an arrhythmic event. If, in the presence of a short V2V interval, the atrial pace to ventricular pace, the PAV is decreased, while the ventricular event to a ventricular pace, the V2V escape is maintained, the device can prevent a string of short V2V intervals caused by conducting an atrial pace. Thus, the Apace, but not the Vpace, is delayed, increasing the V2A interval.

Figure 8:
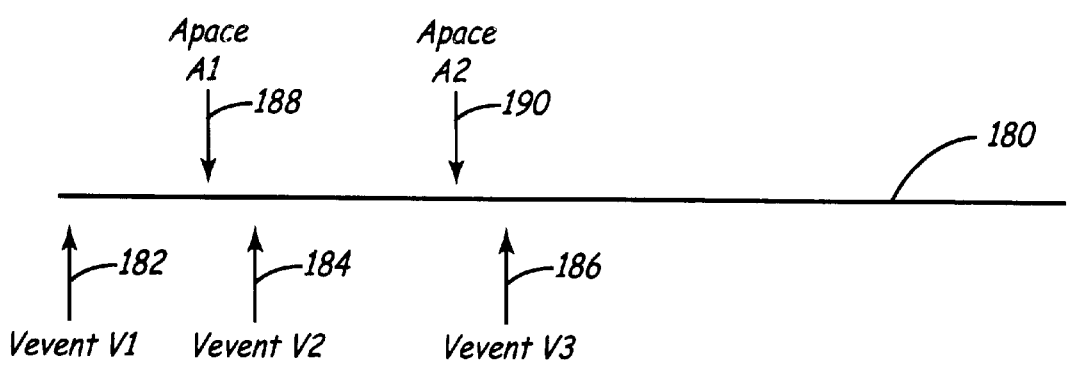
FIG. 8 is a timing diagram of a method adapting the paced atrial to ventricle interval (PAV) to short V2V intervals.

FIG. 8 illustrates the aforementioned situation. FIG. 8 includes a time line 180 having thereon a series of three ventricular events, V1 at 182, V2 at 184, and V3 at 186. Time line 180 also includes a first atrial pacing event, A1 at 188, and a second atrial pacing event, A2 at 190. As may be seen from inspection of FIG. 8, the interval between ventricular event V2 at 184 and ventricular event V3 at 186 is increased relative to the interval between ventricular event V1 at 182 and ventricular event V2 at 184, by decreasing the time from an atrial pace to the next scheduled ventricular pace (PAV), but maintaining the escape time from the previous ventricular event until the current ventricular event (V2V). FIG. 8 thus illustrates how the time from an atrial pace to the next scheduled ventricular pace (PAV) is adapted to short V2V intervals.

Figure 9:
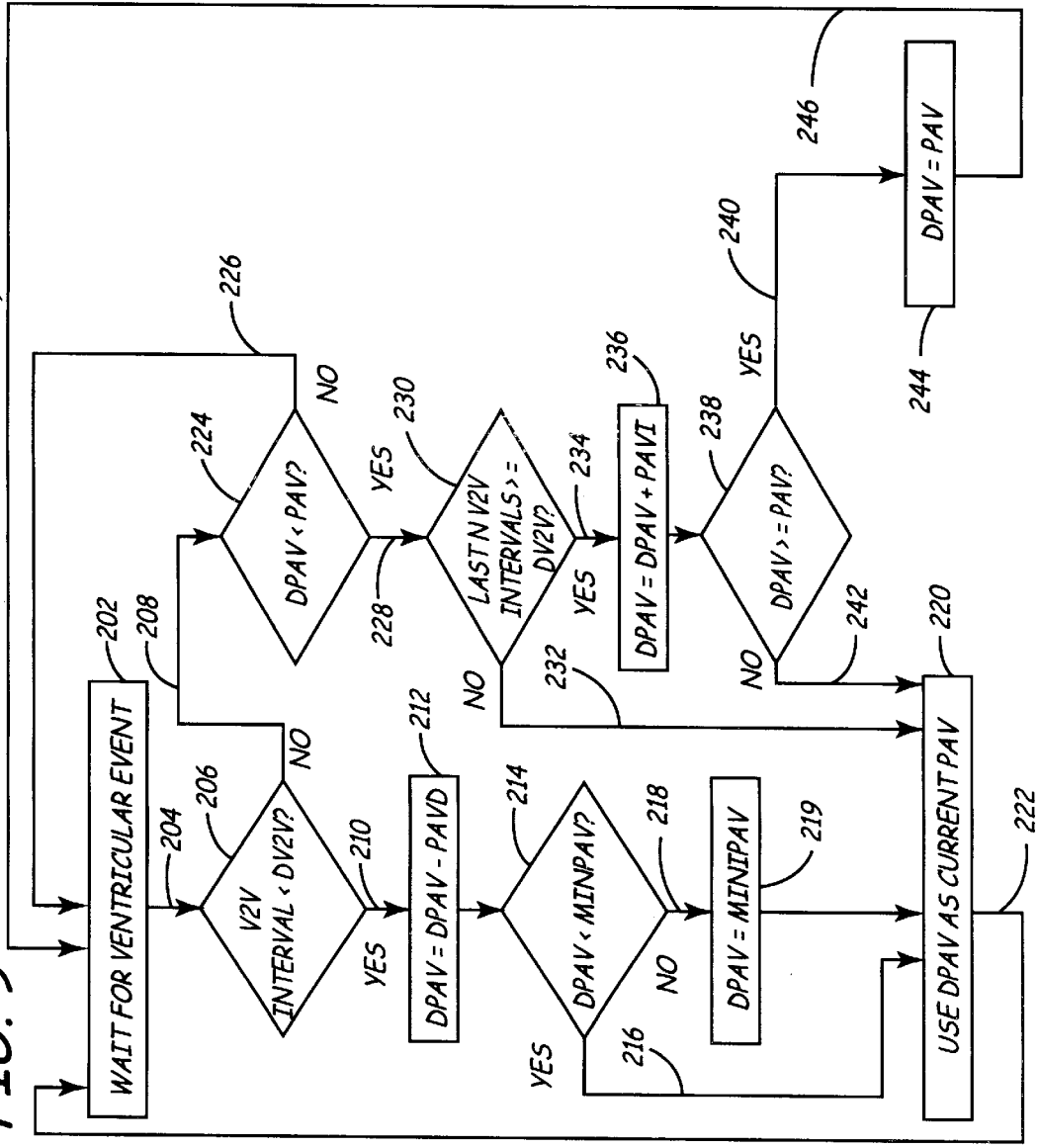
FIG. 9 is a flow chart of a method for adapting the paced arterial to ventricle (PAV) interval in the presence of VSP.

FIG. 9 illustrates a method 200 for adapting the A2V interval. In step 202, the method waits for a ventricular event. Upon sensing a ventricular event, either a V sense or a V pace, but not a VSP, execution follows path 204 to step 206. In decision step 206, a determination is made as to whether the time from the previous ventricular event until the current ventricular event, i.e., the V2V interval, is less than DV2V. DV2V is defined as the minimum V2V interval which ends in a ventricular pace that is long enough such that it does not interfere with detection. If the V2V interval is less than the minimum, DV2V, then execution follows path 210 to step 212. In step 212, the dynamic PAV, DPAV, is decreased by the amount PAVD, the decrement amount used when long V2V intervals occur.

Execution proceeds to decision step 214. In decision step 214, a determination is made as to whether the dynamic PAV (DPAV) is less than MINPAV, i.e., the minimum allowed DPAV value. If the dynamic PAV is not less than the minimum allowed PAV, then execution follows path 218 to step 219. In step 219, the dynamic PAV (DPAV) value is set equal to the minimum allowed PAV value (MINPAV). Execution then proceeds to step 220.

If decision step 214 determines that the dynamic PAV (DPAV) is less than the minimum PAV (MINPAV), then execution follows path 216, to step 220. In step 220, the DPAV value is used as the current PAV in scheduling the next atrial and ventricular pace. After execution of step 220, the method follows path 222 to step 202, to await another ventricular event.

Referring again to step 206, if decision step 206 determines that the time from the previous ventricular event until the current ventricular event, the V2V interval, is not less than the minimum V2V interval, DV2V, then execution follows path 208 to step 224. Decision step 224 determines whether the dynamic PAV (DPAV) is less than PAV, i.e., the time from the atrial pace to the next scheduled ventricular pace. If the dynamic PAV is not less than the PAV, then execution follows path 226 to step 202 to await a ventricular event. If decision step 224 determines that the DPAV value is less than the PAV value, then execution follows path 228 to step 230.

Decision step 230 determines whether all of the last N V2V intervals were greater than or equal to the minimum V2V interval, DV2V, where N can be 10 in some methods. If some of the last N V2V intervals were not greater than or equal to DV2V, then execution follows path 232 to execute step 220, previously discussed. If decision step 230 determines that all of the last N V2V intervals had a value greater than or equal to DV2V, then execution follows path 234 to step 236.

In step 236, the dynamic PAV (DPAV) value is increased by an amount PAVI, where PAVI is the amount used to increment the DPAV when an atrial pace occurs in a short V2V interval. Execution follows to step 238. In decision step 238, a determination is made as to whether the dynamic PAV value (DPAV) is greater than or equal to the time from the atrial pace to the next scheduled ventricular pace, PAV. If the DPAV value is not greater than or equal to the PAV value, then execution follows path 242 to execute step 220, previously discussed. If decision step 238 determines that the DPAV value is greater than or equal to the PAV value, then execution follows path 240 to execute step 244. In step 244, the dynamic PAV value (DPAV) is set equal to the PAV value. Execution then follows path 246 to step 202, to await the next ventricular event.

Figure 10:
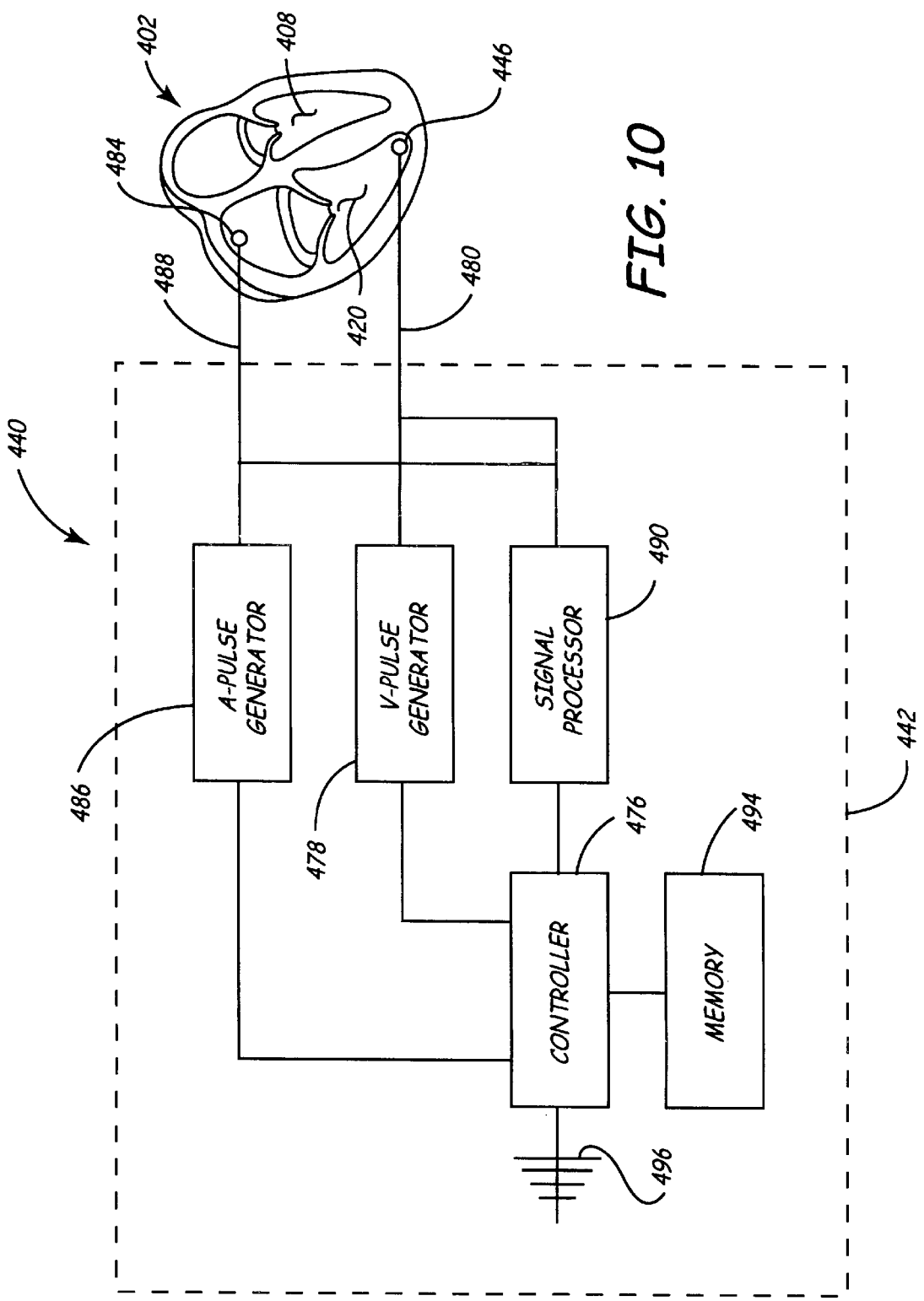
FIG. 10 is a block diagram of a pacing system in accordance with an exemplary embodiment of the present invention.

FIG. 10 is a block diagram of a pacing system 440 in accordance with an exemplary embodiment of the present invention. As shown in FIG. 10, pacing system 440 comprises a pacemaker 442 including a controller 476. Controller 476 may comprise, for example, a microprocessor.

A ventricular pulse generator 478 of pacemaker 442 provides pacing pulses, generated under the control of controller 476, for delivery through a ventricular pulse (VP) generator VP-lead 480 to one or more ventricular electrodes 446. In the embodiment of FIG. 10, a ventricular electrode 446 is shown disposed in a right ventricle 420 of a heart 402. It is to be appreciated that methods and apparatus in accordance with the present invention may be used with multiple chamber pacing. Thus, in some applications, one or more ventricular electrodes may also be located in or near a left ventricle 408 of heart 402. An atrial pulse (AP) generator 486 of pacemaker 442 provides atrial pulses, also generated under the control of controller 476, for delivery through an AP-lead 488 to one or more atrial electrodes 484. Atrial pulse generator 486 and ventricular pulse generator 478 may each include one or more capacitors, and a switching circuit capable of charging the capacitor(s) by coupling the capacitor(s) to an energy source and discharging the capacitor(s) through the electrodes.

Pacemaker 442 also includes a signal processor 490 which may be used to sense and process spontaneous signals from heart 402. For example, signals may be sensed from right atrium 426 via atrial electrode 484. By way of a second example, signals from right ventricle 420 may be sensed via ventricular electrode 446. A method in accordance with the present invention may include the steps of sensing spontaneous signals from heart 402 and determining a desired ventricular pacing rate in response to the sensed ventricle signals. Signal processor 490 may comprise, for example, one or more amplifiers, and one or more filters.

Pacemaker 442 also includes a memory 494. Memory 494 may be used to store operating instructions for controller 476. Memory 494 may also be used to store values in accordance with the present invention. Examples of values which may be stored include a chosen rate and a desired ventricular pacing rate. Pacemaker 442 also includes a telemetry antenna 496. Telemetry antenna may be used, for example, to load instructions and values into memory 494 via controller 476.

Pacing system 440 may be used to implement the methods of the present invention using standard methods well known to those skilled in the art. The methods can be expressed as complete programs or other logical systems, for example, any combinations of Boolean logic, gates and timers. The logic and/or programs may reside within memory 494 and be executed by controller 476.

Figure 11:
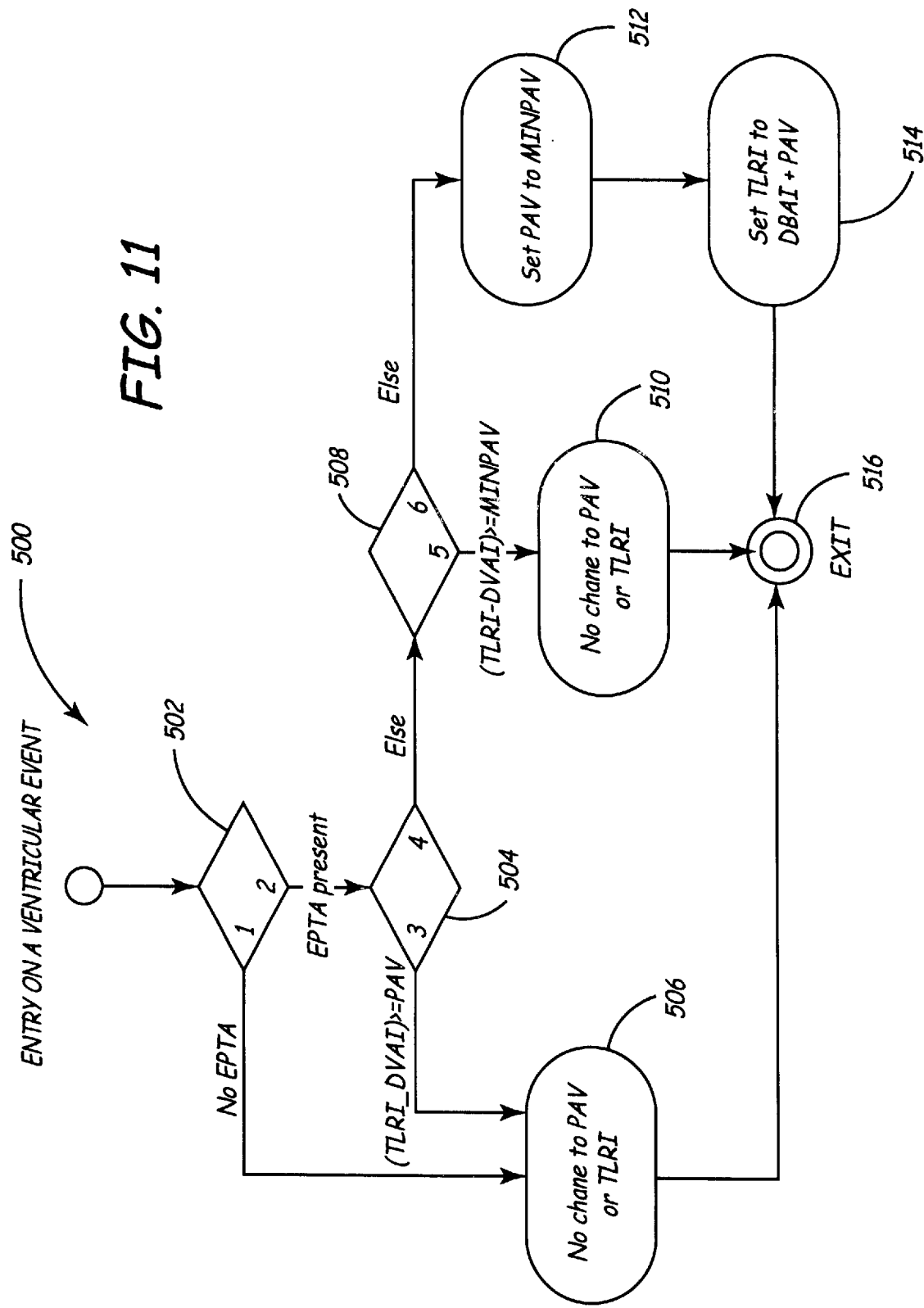
FIG. 11 is a block diagram of a pacing system in accordance with an improved exemplary embodiment of the present invention.

Referring to FIG. 11, the software system 500 is initiated by an entry of a ventricular event. Under decision step 502, evidence of possible tachyarrhythmia is checked. If evidence of possible tachyarrhythmia is confirmed, the logic proceeds to decision step 504 where if the difference between TLRI (the time between an atrial pace and the next scheduled atrial pace) and DVAI (the ventricular to atrial interval required to insure an atrial pace does not interfere with tachyarrhythmias detection) is greater or equal to PAV (the time between an atrial pace and the scheduled ventricular pace), then no change to either the PAV or the TLRI is recommended and the software logic terminates at logic step 516. In the alternate, the logic step may proceed to decision step 508 where, if the difference between TLRI and DVAI is greater than or equal to a minimum PAV, then the PAV is set to the difference between TLRI and DVAI and the logic step terminates at 516. Further, if the difference between TLRI and DVAI is greater than or equal to the minimum PAV, then the PAV is set to the minimum PAV. Thereafter, the TLRI is set equal to the sum of DVAI and PAV and the process terminates at step 516.

Accordingly, the algorithm of the present invention adjusts PAV to minimize the impact of atrial pacing when evidence of a tachyarrhythmia is detected. If the change in PAV is not sufficient to ensure that atrial pacing does not interfere with tachyarrhythmia detection, then the algorithm would adjust the overall pacing rate, PLRI. Further, in the presence of a possible tachyarrhythmia, the time between the ventricular event, either paced or sensed, and the next scheduled atrial pace VAI is checked to ensure that atrial pace does not interfere with the detection of tachyarrhythmia. This is accomplished by adjusting the time between the atrial pace and the next scheduled ventricular pace, PAV, in addition to adjusting the time between an atrial event and the next scheduled atrial pace.

What is claimed is:

1. A device-implemented software system operating to monitor, control and adjust a detection window comprising:

means for checking evidence of tachyarrhythmias;

means for computing values between TLRI and DVAI;

means for setting PAV based on results obtained from said means for computing values; and means for setting the TLRI equal to a sum of the DVAI and PAV;

said means for checking, said means for setting PAV and said means for setting the TLRI being in operable logic control of said software system.

2. The software system of clam 1 wherein said means for checking tachyarrhythmias includes means for entering a ventricular event.

3. The software system of claim 1 wherein said means for computing values includes means for calculating the difference between the TLRI and the DVAI.

4. The software system of claim 1 wherein said means for setting PAV includes means for reviewing said difference between the TLRI and the DVAI and comparing the difference value with the PAV.

5. The software system of claim 1 wherein said means for setting the TLRI includes means for taking a sum of DVAI and PAV.

6. A method of adjusting PAV to minimize the input of atrial pacing in a detected tachyarrhythmias episode, the method comprising:

monitoring evidence of possible tachyarrhythmia;

comparing the difference between TLRI and DVAI with PAV if evidence of possible tachyarrhythmias is confirmed;

comparing the difference between TLRI and DVAI with minimum PAV if the difference between TLRI and DVAI is less than PAV;

setting PAV to the minimum PAV if the difference between TLRI and DVAI is less than the minimum PAV; and setting the TLRI equal to the sum of DVAI and PAV.

7. The method of claim 6 wherein the method of comparing the difference between TLRI and DVAI with PAV includes indicating no change to PAV or TLRI if the difference is greater than or equal to PAV.

8. The method of claim 6 wherein the method of comparing the difference between TLRI and DVAI with minimum PAV includes setting PAV equal to the difference between TLRI and DVAI if that difference is greater or equal to minimum PAV.

9. The method of claim 6 wherein said method of setting the TLRI equal to the sum of DVAI and PAV is subsequent to setting PAV equal to minimum PAV.

* * * * *